US008506989B2

(12) United States Patent
Gastner et al.

(10) Patent No.: US 8,506,989 B2
(45) Date of Patent: Aug. 13, 2013

(54) PREPARATION COMPRISING A CREATINE COMPONENT, METHOD FOR THE PRODUCTION THEREOF, AND THE USE THEREOF

(75) Inventors: Thomas Gastner, Engelsberg (DE); Frauke Warrikoff, Frankfurt (DE); Barbara Nieβ, Trostberg (DE); Josef Fuest, Trostberg (DE)

(73) Assignee: AlzChem Trostberg GmbH, Trostberg (DE)

( * ) Notice: Subject to any disclaimer, the term of this patent is extended or adjusted under 35 U.S.C. 154(b) by 435 days.

(21) Appl. No.: 12/809,293

(22) PCT Filed: Dec. 18, 2008

(86) PCT No.: PCT/EP2008/010851
§ 371 (c)(1),
(2), (4) Date: Apr. 1, 2011

(87) PCT Pub. No.: WO2009/083169
PCT Pub. Date: Jul. 9, 2009

(65) Prior Publication Data
US 2012/0141383 A1    Jun. 7, 2012

(30) Foreign Application Priority Data
Dec. 21, 2007  (DE) .................. 10 2007 062 288

(51) Int. Cl.
| *A61K 8/02* | (2006.01) |
| *A61K 9/14* | (2006.01) |
| *A61K 9/20* | (2006.01) |
| *A61K 9/48* | (2006.01) |
| *A61K 31/66* | (2006.01) |
| *A61K 31/655* | (2006.01) |
| *A61K 31/155* | (2006.01) |
| *A61K 31/195* | (2006.01) |
| *A61K 31/197* | (2006.01) |
| *A61K 31/198* | (2006.01) |
| *A61K 31/205* | (2006.01) |

(52) U.S. Cl.
USPC ......... 424/439; 424/401; 424/441; 424/451; 424/464; 424/489; 514/114; 514/150; 514/151; 514/554; 514/561; 514/565

(58) Field of Classification Search
USPC ............. 424/401, 439, 441, 451, 464, 489; 514/114, 150, 151, 554, 561, 565
See application file for complete search history.

(56) References Cited

U.S. PATENT DOCUMENTS

| 5,863,939 | A | 1/1999 | Pischel et al. |
| 5,908,864 | A | 6/1999 | Casey |
| 5,925,378 | A | 7/1999 | Carnazzo |
| 5,968,544 | A | 10/1999 | Howard et al. |
| 6,093,746 | A | 7/2000 | Uchida et al. |
| 6,172,111 | B1 | 1/2001 | Pischel et al. |
| 6,274,161 | B1 | 8/2001 | Howard et al. |
| 6,413,552 | B1 | 7/2002 | Stoll |
| 6,706,764 | B2 | 3/2004 | Beal et al. |
| 7,226,947 | B1 | 6/2007 | Wallimann et al. |
| 2002/0131987 | A1 | 9/2002 | Carnazzo |
| 2003/0215506 | A1 | 11/2003 | Kurtz |
| 2006/0073189 | A1 | 4/2006 | Pinney et al. |
| 2007/0281996 | A1 | 12/2007 | Gao et al. |
| 2008/0161387 | A1 | 7/2008 | Gastner et al. |
| 2010/0056633 | A1 | 3/2010 | Gastner |

FOREIGN PATENT DOCUMENTS

| DE | 197 07 694 A1 | 8/1998 |
| DE | 10 355 711 A1 | 6/2005 |
| DE | 10 2005 009 990 A1 | 9/2006 |
| DE | 10 2005 061 765 A1 | 11/2006 |
| DE | 10 2006 035 801 A1 | 4/2007 |
| DE | 10 2006 050 931 A1 | 4/2008 |
| EP | 0 911 026 A1 | 4/1999 |
| EP | 1 051 914 A1 | 11/2000 |
| WO | WO 96/14063 A1 | 5/1996 |
| WO | WO 98/28263 A1 | 7/1998 |
| WO | WO 01/89476 A1 | 11/2001 |
| WO | WO 2004/073420 A1 | 9/2004 |
| WO | WO 2006/015774 A1 | 2/2006 |
| WO | WO 2006/122809 A1 | 11/2006 |

OTHER PUBLICATIONS

Schoch, et al. "The Regulation and Expression of the Creatine Transporter: A Brief Review of Creatine Supplementation in Humans and Animals", *J. Int'l. Soc. Sports Nutrit.* 3(1) (2006) pp. 60-66.
Chilibeck, et al. "Creatine monohydrate and resistance training increase bone mineral content and density in older men", *J. Nutrition, Health & Aging* (2004), pp. 1-4.
Francaux, et al. "Effect of Exogenous Creatine Supplementation on Muscle OCr Metabolism", *Int J. Sports Med.* 21 (2000), pp. 139-145.
Gerber, et al. "Stimulatory effects of creatine on metabolic activity, differentiation and mineralization of primary osteoblast-like cells in monolayer and micromass cell cultures", *Eur. Cells and Materials*, 10 (2005), pp. 8-22.

(Continued)

*Primary Examiner* — James H. Alstrum-Acevedo
(74) *Attorney, Agent, or Firm* — Fulbright & Jaworski LLP

(57) ABSTRACT

The invention relates to a preparation comprising a creatine component, which has excellent bio-availability and leads to improved creatine retention in the human and animal body. The present invention further relates to a method for the production of said preparation, and to the use thereof as a nutritional supplement, functional food, animal feed additive, pharmaceutical, and as an additive for cosmetic and dermatologic formulations.

19 Claims, 1 Drawing Sheet

(56) References Cited

OTHER PUBLICATIONS

Green, et al. "Carbohydrate ingestion augments skeletal muscle creatine accumulation during creatine supplementation in humans", *Amer. Phys. Soc.* 1996, pp. 821-826.

Greenhaff, Paul L. "Factors Modifying Creatine Accumulation in Human Skeletal Muscle", Creatine, 2000 Kluwer Academic Publ, and Fondazione G, Lorenzini, pp. 75-82.

Klivenyi, et al. "Neuroprotective effects of creatine in a transgenic animal model of amyotropic lateral sclerosis", *Nature Med.* 5, No. 3. (1999), pp. 347-350.

Rae, et al. "Oral creatine monohydrate supplementation improves brain performance: a double-blind, placebo-controlled, cross-over trial", *Proc. R. Soc. Lond. B* 270. (2003) pp. 2147-2150.

Sestili, et al. "Creatine supplementation affords cytoprotection in oxidatevely injured cultured mammalian cells via direct antioxidants activity", *Free Radical Biol. & Med.* 40 (2006), pp. 837-849.

Speer, et al. "Creatine transporters: A reappraisal", *Mol and Cell. Biochem.* 256/257 (2004), pp. 407-424.

Steenge, et al. "Protein- and carbohydrate-induced augmentation of whole body creatine retention in humans", *J. Appl. Physiol.* 89 (2000), pp. 1165-1171.

Watanabe, et al. "Effects of creatine on mental fatigue and cerebral hemoglobin oxgenation", *Neurosci Res.* 42 (2002), pp. 279-285.

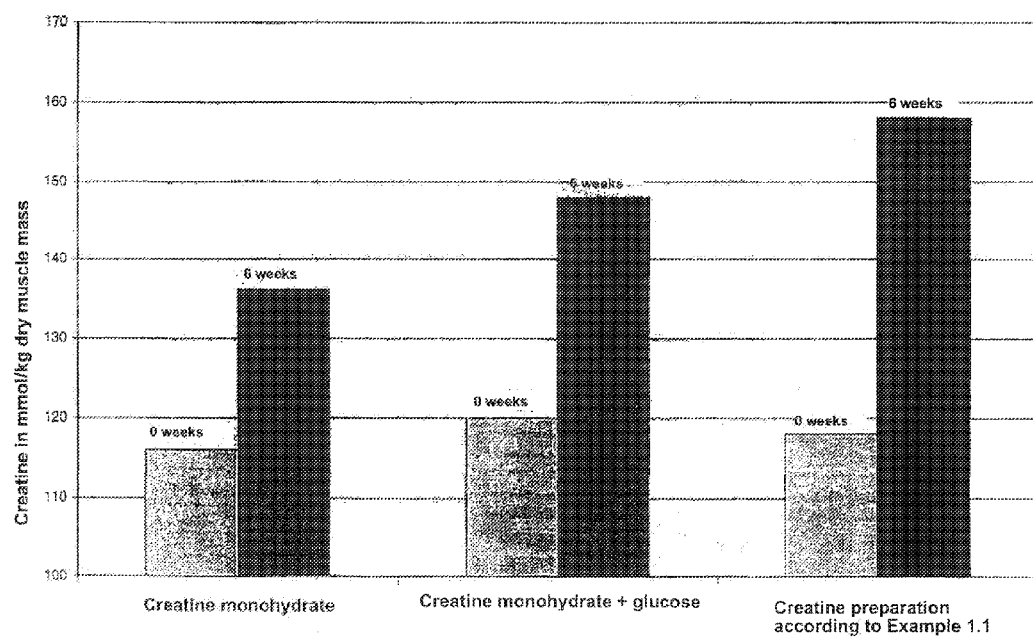

PREPARATION COMPRISING A CREATINE COMPONENT, METHOD FOR THE PRODUCTION THEREOF, AND THE USE THEREOF

RELATED APPLICATIONS

This application is a §371 application of PCT/EP2008/010851 filed Dec. 18, 2008, which claims priority from German Patent Application No. 10 2007 062 288.2 filed Dec. 21, 2007.

The present invention provides a preparation comprising a creatine component, which has excellent bioavailability and leads to improved creatine retention in the human and animal body. The present invention furthermore relates to a method for producing this preparation and to the use thereof as a nutritional supplement, functional foodstuff, feedstuff additive, medicament and as an additive for cosmetic and dermatological formulations.

The ergogenic action of creatine has been the subject of systematic investigation since the late 1970's. To date, more than 300 sports-related studies have been carried out, some 80% of these studies demonstrating significant positive effects of creatine on muscle mass, muscle power, lean body mass and performance at maximum, short-duration muscle exertion in various types of sport. Today, creatine monohydrate is the most significant nutritional supplement in the field of sports.

Further interesting properties of creatine have only recently been discovered. For instance, two studies have demonstrated significant positive effects of oral creatine supplementation on brain performance and powers of concentration (Rae, Caroline et al.: Oral creatine monohydrate supplementation improves brain performance: a double-blind, placebo-controlled, cross-over trial. Proceedings of the Royal Society of London, Series B: Biological Sciences (2003), 270(1529), 2147-2150; Watanabe, Airi et al.: Effects of creatine on mental fatigue and cerebral hemoglobin oxygenation. Neuroscience Research (Oxford, United Kingdom) (2002), 42(4), 279-285).

It has furthermore been possible to show that creatine has antioxidant and neuroprotective properties and may thus also be used to prevent cell damage by environmental factors (Sestili, Piero et al.: Creatine supplementation affords cytoprotection in oxidatively injured cultured mammalian cells via direct antioxidant activity. Free Radical Biology & Medicine (2006), 40(5), 837-849; P. Klivenyi et al.: Neuroprotective effects of creatine in a transgenic animal model of amyotrophic lateral sclerosis. Nature Medicine 5, 347-350 (1999)). Creatine will therefore in future also become increasingly significant in the anti-ageing field.

The positive effects of creatine are currently also under intense investigation in the medical field, creatine being in clinical phase 3 for the treatment of Parkinson's disease and amyotrophic lateral sclerosis (ALS) and in phase 2 for Huntington's disease (EP 804 183 B1). The successful use of creatine as a therapeutic agent against asthma has already been reported (EP 911 026 B1). Creatine has exhibited positive effects in osteogenesis both in vitro and in vivo. Use for strengthening bone and for treating and preventing degenerative bone and cartilage diseases such as for instance osteoporosis has been investigated and yielded very positive results (EP 1 100 488 B1; Gerber, I. et al.: Stimulatory effects of creatine on metabolic activity, differentiation and mineralization of primary osteoblast-like cells in monolayer and micromass cell cultures. European Cells and Materials (2005), 10, 8-22; Chilibeck, P. D. et al.: Creatine monohydrate and resistance training increase bone mineral content and density in older men. Journal of Nutrition, Health & Aging (2005), 9(5), 352-355).

It is furthermore known that creatine supplementation leads to an increase in body mass. This is firstly attributable to increased uptake of water into muscle. In the long term, however, creatine leads indirectly to an increase in muscle mass by increased protein synthesis or reduced protein catabolism in the myofibrils (Int. J. Sports Med. 21 (2000), 139-145). The outcome is accordingly an elevated lean body mass.

In addition to creatine itself, namely creatine monohydrate, numerous creatine salts, such as creatine ascorbate, citrate, pyruvate and others, have in the meantime likewise proved to be suitable nutritional supplements. European Patent EP 894 083 and German published patent application DE 197 07 694 A1 may be mentioned as representative prior art at this point.

The metabolism and mode of action of creatine have been very thoroughly investigated. Biosynthesis starts from glycine and L-arginine. In mammals it is primarily in the kidneys, but also in the liver and pancreas, that the guanidino group of L-arginine is cleaved by the enzyme aminotransferase and an N—C—N group is transferred onto glycine. As a result, L-arginine is converted into L-ornithine. In the next step, which primarily takes place in the liver in vertebrates, the guanidinoacetic acid formed is converted into creatine with the assistance of the enzyme transmethylase. S-Adenosylmethionine here serves as the methyl group donor. The creatine then diffuses into the bloodstream, which transports it to the target organs. Transport through the cell membrane into the cells here proceeds by means of a specific NaCl-dependent creatine transporter (Speer O., Neukomm L. J., Murphy R. M., Zanolla E., Schlattner U., Henry H., Snow R. J., Wallimann T. Creatine transporters: a reappraisal. Mol. Cell. Biochem. 2004 January-February; 256-257(1-2):407-24).

Creatine plays an important part in cellular energy metabolism, constituting as high-energy phosphocreatine a significant muscular energy reserve in addition to adenosine triphosphate (ATP). In the resting state of the muscle, ATP can transfer a phosphate group onto creatine, so forming phosphocreatine, which is then in direct equilibrium with ATP. During muscular work, it is of vital importance to replenish ATP stores as rapidly as possible. Phosphocreatine is available for this purpose during the first seconds of maximum muscle load; this substance is capable in a very rapid reaction of transferring a phosphate group onto adenosine diphosphate by the enzyme creatine kinase, so reforming ATP. This is also known as the Lohmann reaction.

Creatine furthermore has an important function in the transmission of energy in the cell. The "creatine shuttle system" transports energy from the mitochondria to those locations in the cell where energy is required.

In the event of intense, relatively long-lasting muscular work, the creatine stores naturally present in the body are rapidly depleted. For this reason, targeted administration of creatine has had a positive effect on endurance and performance in particular for competitive athletes, any undesired accumulation phenomena in the body or disadvantageous breakdown products being unknown. The reason for this is that, in the event of excessive intake, creatine is excreted by the body via the kidneys. Furthermore, creatine is converted at a constant rate into the cyclic breakdown product creatinine, which is likewise excreted via the kidneys so providing a second metabolic breakdown pathway.

Uptake of creatine from the intestine and transport into the muscles is controlled by an NaCl-dependent creatine transporter and may be promoted by the simultaneous intake of carbohydrates and proteins. It has here been found that, in comparison with the sole intake of creatine, the combination of creatine and carbohydrates can lead to a 60% greater rise in creatine content in the muscle (Green A. L., Hultman E., Macdonald I. A., Sewell D. A., Greenhaff P. L. Carbohydrate ingestion augments skeletal muscle creatine accumulation during creatine supplementation in humans. Am. J. Physiol. 1996 November; 271 (5 Pt 1):E821-6). It has been possible to show that the release of insulin plays an important part in the uptake of creatine into the muscle cells. There is a linear relationship between the increase in creatine concentration in the muscles and the secreted quantity of insulin (Steenge G. R., Simpson E. J., Greenhaff P. L. Protein- and carbohydrate-induced augmentation of whole body creatine retention in humans. J. Appl. Physiol. 2000 September; 89(3):1165-71).

Further formulations have been suggested for improving the uptake of creatine into the body. Patent application DE 10 2006 050 931.5 accordingly describes a solid or aqueous alkaline preparation comprising a creatine component, which contains a buffer system which establishes a pH value of 8.0 to 12.0.

US 2003215506 claims a formulation which enhances the creatine transport, said formulation containing IGF-1 modulating substances, in particular proteins, colostrum or recombinant IGF-1.

Apart from its undisputed positive physiological characteristics, creatine does, however, also have the disadvantage that it does not have any marked stability in corresponding aqueous solutions, creatine cyclising by the elimination of water to yield creatinine. The rate of cyclisation is dependent on the pH value of the solution and temperature, with concentration playing no part. Conversion to creatinine proceeds rapidly in particular in the acidic pH range between 3 and 4. The rapid breakdown of creatine in this medium virtually rules out the use of aqueous or moist formulations for human and animal nutrition. Just the stomach's pH value of 1 to 2 can lead to appreciable breakdown of creatine to creatinine depending on residence time (Greenhaff, P. L.: Factors Modifying Creatine Accumulation in Human Skeletal Muscle. In: Creatine. From Basic Science to Clinical Application. Medical Science Symposia Series Volume 14, 2000, 75-82).

The stated disadvantages of the prior art with regard to uptake from the intestine and transport into the target tissue and with regard to the stability of creatine have given rise to the object of the present invention of providing preparations which protect creatine better than previously from breaking down to creatinine in the stomach and then lead to improved uptake from the intestine. One vital factor, however, is optimum uptake and thus retention of the creatine in the target tissue. A further object was thus to ensure that the creatine absorbed from the intestine is optimally taken up into the target tissue and is not excreted as such via the kidneys or converted into creatinine, which is useless to the body and must likewise be excreted from the body via the kidneys. The preparations should furthermore have good organoleptic characteristics. The preparations according to the invention should furthermore exhibit improved bioavailability in dermatological and cosmetic preparations and thus assist with improved uptake of the creatine component into the skin.

Said object is achieved by the provision of a preparation comprising a creatine component and a buffer system, the buffer system consisting of at least one sodium salt of an organic acid and the preparation having a pH value of 2.5 to 7.9.

It has been possible to show that these preparations are capable of completely achieving the object of the invention, namely that the buffer system protects creatine better from conversion into creatinine in the stomach than previously. It has surprisingly been found that the new formulations lead to distinctly better uptake from the intestine, exhibit distinctly higher bioavailability and are thus better taken up into the target tissue. The preparation according to the invention moreover has very good organoleptic characteristics.

The creatine component preferably comprises creatine, creatine monohydrate, guanidinoacetic acid, creatine esters, creatinol, creatinol O-phosphate or mixtures of at least two of these compounds. Guanidinoacetic acid, creatine esters, creatinol and creatinol O-phosphate are known to be converted into creatine in the body and in this manner are able to perform their action. Creatine esters which may in particular be used are creatine methyl ester and creatine ethyl ester. Creatine monohydrate and guanidinoacetic acid should be regarded as particularly preferred creatine components for the purposes of the invention.

In a further preferred embodiment, the creatine component is a salt, an addition or complex compound of this component, preferably with malic acid, ascorbic acid, succinic acid, pyruvic acid, fumaric acid, aspartic acid, adipic acid, gluconic acid, α-ketoglutaric acid, tartaric acid, α-lipoic acid, oxalic acid, pyroglutamic acid, 3-nicotinic acid, maleic acid, sulfuric acid, acetic acid, formic acid, phosphoric acid, hydrochloric acid, 2-hydroxybenzoic acid, L-carnitine, acetyl-L-carnitine, taurine, betaine, choline and methionine.

With regard to the sodium salt of an organic acid present in the buffer system, particularly suitable organic acids have in particular proven to be malic acid, ascorbic acid, succinic acid, pyruvic acid, fumaric acid, adipic acid, aspartic acid, gluconic acid, α-ketoglutaric acid, α-lipoic acid, tartaric acid, oxalic acid, pyroglutamic acid, 3-nicotinic acid, citric acid, maleic acid, acetic acid, formic acid, 2-hydroxybenzoic acid, sorbic acid and isoascorbic acid.

It should be considered essential to the invention for the buffer system to establish a pH value of 2.5 to 7.9 and preferably of 5.0 to 7.0. The preferred buffer system provided by the present invention is a mixture of trisodium citrate and/or disodium citrate and/or monosodium citrate, with a mixture of trisodium citrate and disodium citrate being particularly preferred. The ratio of trisodium citrate and disodium citrate may be freely selected over wide ranges, said ratio preferably being selected such that the pH value of the formulation is established at 2.5 to 7.9, preferably at 5.0 to 7.0. It is here advantageous that, if the mixture ratio is correctly selected, there is virtually no restriction on the amount which may be introduced. For instance, when a 1:1 mixture is used, a pH value of 6.4 is inevitably established, this being independent of the total quantity of buffer introduced.

In this way, a pH value acceptable from an organoleptic standpoint may be established and at the same time the creatine is surprisingly well protected from the influence of acids, in particular of gastric acid, so avoiding conversion into creatinine. The excellent action of the buffer system, which largely prevents any breakdown of creatine into creatinine, could not in any way be predicted in the claimed pH range.

The formulation is not limited with regard to the buffer component, there in particular being no limit on the quantity of buffer component which may be present in the preparation. For reasons of nutritional physiology, however, recommended quantities are between 0.1 and 90.0 wt. %, relative to the total weight of the preparation. Quantities of between 2.5 and 50.0 wt. % and in particular of 15.0 to 40.0 wt. % relative to the total weight of the preparation are particularly preferred.

It has surprisingly been found on use of the described buffer systems not only that they lead to reduced breakdown of creatine in the stomach, but that uptake of the administered creatine into the cells is also improved. It has accordingly been possible to demonstrate experimentally that the formulations according to the invention lead to a distinctly greater rise in creatine concentrations in the muscle than is the case when creatine monohydrate is used.

In this connection, it has surprisingly been found that the sodium content of the formulation has a decisive influence on the bioavailability and the uptake of creatine into the cells. The use of a mixture of creatine and sodium salts for improving the uptake of creatine into the muscle has not hitherto been described and offers distinct advantages over the previous practice of using elevated carbohydrate or protein doses. A molar ratio of creatine component to sodium ions of 1:1-10, in particular of 1:1-3 and particularly preferably of 1:2-3 has proven advantageous.

The present invention thus optionally provides incorporating, in addition to the buffer system, at least one further sodium salt, which is preferably physiologically acceptable, into the creatine preparations. Sodium chloride, sodium sulfate, sodium acetate, sodium adipate, sodium citrate, sodium gluconate, sodium ascorbate, sodium pantothenate, sodium tartrate and sodium lactate or mixtures of these salts may preferably be considered for this purpose.

The proportion of these sodium salts is relatively non-critical, but it has proven particularly advantageous to use these further sodium salts in a quantity of 0.1 to 75.0 wt. %, in particular of 1.0 to 55.0 wt. % and particularly preferably of 5.0 to 10.0 wt. %, relative to the total weight of the preparation.

Using the described buffer systems would thus appear to be ideal, since on the one hand the stability of the creatine to acids is increased and thus the breakdown of creatine in the stomach is avoided. Moreover, the sodium ions present improve uptake into the cells, it also being possible to enhance this effect still further by the addition of further sodium salts.

According to a preferred embodiment, the preparation according to the invention contains still further physiologically active compounds, such as for example carbohydrates, fats, amino acids, proteins, vitamins, minerals, trace elements and the derivatives and mixtures thereof. Particularly preferred additional physiologically active compounds are those selected from the group of carbohydrates, saturated or unsaturated fatty acids, saturated or unsaturated triglycerides, amino acids, amino acid derivatives such as taurine, carnitine, glutathione or proteins such as for example gelatin, vitamins, vitaminoids such as for example ubiquinones, α-lipoic acid, inositol, phospholipids, minerals and trace elements and mixtures thereof.

The addition of α-lipoic acid to the preparation serves to improve bioavailability.

The present invention also provides a method for producing the preparations according to the invention, in which the creatine component, preferably in powder form, is initially introduced, at least one buffer system consisting of a mixture of a weak acid and the corresponding base is incorporated and further sodium salts, physiologically active compounds and/or α-lipoic acid are optionally added. In a preferred embodiment, incorporation proceeds homogeneously. It is furthermore preferred for the weak acid to be an organic acid and for the corresponding base to be a sodium salt of the weak acid.

The present invention moreover claims the use of the creatine preparation according to the invention as a nutritional supplement, functional foodstuff, feedstuff additive and/or medicament.

Powders, granular products, pastilles, capsules, tablets, effervescent tablets, solutions, syrups and/or gel products have proven to be particularly suitable administration forms. Depending on the particular specific application, it may here be highly recommended to use the creatine preparation in combination with other active ingredients having a physiological action.

The preparations according to the invention also have the described positive effects in animals, such that use in animals is also provided. If the described creatine formulations are used as a feedstuff additive, administration should in particular be regarded as preferred for breeding and fattening animals and animals in competitive sport and in this connection particularly preferably for pigs, horses, poultry and fish, with use as a substitute for animal and/or fish meal and products produced therefrom having proved to be particularly suitable. Substitution may here be partial or complete.

The novel creatine preparations may furthermore also be used as a nutritional supplement or dietary component for pets, such as dogs, cats and birds.

It has proven particularly advantageous for the preparations to contain the creatine component in daily doses of 5 mg to 400 mg, preferably of 10 to 250 mg and particularly preferably of 30 mg to 100 mg per kg of body weight.

The proportion in the entire preparation may vary over wide ranges. The creatine component may be used in quantities of to 90.0 wt. %, in particular of 30 to 80.0 wt. % and particularly preferably of 40.0 to 60.0 wt. %, relative to the total weight of the preparation. The daily doses may be taken as an individual dose or in several doses divided over the day. It has proved advantageous to divide the preparation into at least two individual doses over the day.

In line with known fields of application for creatine, the preparations may also be used for the purposes of the present invention in cosmetic or dermatological preparations. The buffer system and the sodium ions here provide a distinctly improved uptake profile into the skin. Apart from the buffer system, it has also proven advantageous additionally to add a source of chloride ions, in particular sodium chloride, to the cosmetic or dermatological preparations. In contrast with oral intake of the preparation, where the chloride ions are provided by the gastric acid, this optimises uptake into the skin. Preferred preparations should be considered those which assume the form of creams, lotions, sprays, mousses, aqueous or aqueous-ethanolic solutions, impregnation media for wipes, anhydrous or hydrous sticks or microemulsions. Topical applications should be considered very particularly preferred.

Overall, the proposed preparations and the use thereof constitute a further development of the prior art in terms of an increase in the stability of creatine preparations and a substantial improvement in bioavailability, the preparations furthermore being distinguished by good organoleptic characteristics.

Use not only as a nutritional supplement, functional foodstuff and feedstuff but also in dermatological and cosmetic formulations is here provided.

The following Examples illustrate the advantages of the present invention.

EXAMPLES

1. Nutritional Supplements

Typical compositions whose constituents are introduced at room temperature into 500 ml of fruit juice, water, yogurt, and/or whey are listed below.

1.1 3,000 mg creatine monohydrate
   950 mg trisodium citrate
   1050 mg disodium citrate
1.2 1000 mg creatine monohydrate
   1430 mg sodium gluconate
   1200 mg gluconic acid
1.3 1500 mg creatine monohydrate
   1800 mg sodium malate
   1000 mg sodium hydrogenmalate
   500 mg guanidinoacetic acid
   500 mg betaine
   300 mg α-lipoic acid
   400 mg $(MgCO_3)_4 \cdot Mg(OH)_2 \cdot 5H_2O$=approx. 100 Mg
1.4 1,500 mg creatine monohydrate
   900 mg sodium succinate
   600 mg sodium hydrogensuccinate
   1,000 mg glucosamine
   300 mg chondroitin sulfate
   500 mg methionine 2. Feedstuffs 2.1 A formulation consisting of 2 kg of creatine monohydrate, 5 kg of inulin, 600 g of disodium citrate and 655 g of trisodium citrate was introduced into 100 kg of a typical formulation for dietary supplement feed pellets for horses.

2.2 The following formulation was homogeneously introduced as a masterbatch into 500 g of a conventional commercial canned cat food: 3,000 mg of creatinol sulfate, 3,000 mg of creatine monohydrate, 40 mg of magnesium stearate, 25 mg of carboxymethylcellulose and 135 mg of lactose, 500 mg of gluconic acid and 1000 mg of sodium gluconate.

3. Preparations for Cosmetic Creams 3.1 0.6% of creatine monohydrate, 0.19% of disodium citrate, 0.21% of trisodium citrate and 0.2% of sodium chloride were homogeneously introduced into a conventional commercial water-in-oil base cream.
   The cream is inter alia suitable for treating skin states due to sensitivity, deficiency and hypoactivity and against premature skin ageing and negative skin changes brought about by environmental conditions.

4. Bioavailability

Three groups of in each case twenty human test subjects were assembled in such a way that approximately the same average initial creatine values in dry muscle mass were present in all of the groups.

Over six weeks, a preparation according to the invention of Example 1.1, creatine monohydrate or creatine monohydrate and 75 g of glucose were administered daily to the three groups. The dose was here selected such that each test subject had a daily intake of 3.0 g of pure creatine monohydrate. The creatine content in the muscle was measured by muscle biopsy immediately before the study and six weeks after intake. The results are shown in FIG. 1.

The invention claimed is:
1. A preparation comprising 30-80 wt. % of a creatine component relative to the total weight of the preparation and a buffer system, wherein the buffer system comprises 2.5 to 50 wt. % of at least one sodium salt of an organic acid relative to the total weight of the preparation, and wherein the buffer system establishes a pH value of 2.5 to 7.9, and wherein a molar ratio of creatine component to sodium ions is from 1:1 to 1:10.

2. A preparation according to claim 1, wherein the organic acid is selected from the group consisting of malic acid, ascorbic acid, succinic acid, pyruvic acid, fumaric acid, adipic acid, aspartic acid, gluconic acid, α-ketoglutaric acid, α-lipoic acid, tartaric acid, oxalic acid, pyroglutamic acid, 3-nicotinic acid, citric acid, maleic acid, acetic acid, formic acid, 2-hydroxybenzoic acid, sorbic acid and isoascorbic acid.

3. A preparation according to claim 1, wherein the sodium salt is selected from the group consisting of trisodium citrate, disodium citrate and monosodium citrate.

4. A preparation according to claim 1, wherein the sodium salt comprises trisodium citrate and disodium citrate.

5. A preparation according to claim 1, wherein the creatine component comprises at least one member selected from the group consisting of creatine, creatine monohydrate, guanidinoacetic acid, creatine esters, creatinol and creatinol O-phosphate.

6. A preparation according to claim 1, wherein the creatine component comprises at least one of a salt, an addition compound or a complex compound of the creatine component.

7. A preparation according to claim 6, wherein the creatine component is formed with malic acid, ascorbic acid, succinic acid, pyruvic acid, fumaric acid, aspartic acid, adipic acid, gluconic acid, α-ketoglutaric acid, tartaric acid, α-lipoic acid, oxalic acid, pyroglutamic acid, 3-nicotinic acid, maleic acid, sulfuric acid, acetic acid, formic acid, phosphoric acid, hydrochloric acid, 2-hydroxybenzoic acid, L-carnitine, acetyl-L-carnitine, taurine, betaine, choline or methionine.

8. A preparation according to claim 1, wherein the creatine component is provided for administration in a daily dose of 5 mg to 400 mg per kg of body weight.

9. A preparation according to claim 1, wherein the preparation further comprises a physiologically active compound selected from the group consisting of a carbohydrate, a saturated fatty acid, an unsaturated fatty acid, a saturated triglyceride, an unsaturated triglyceride, an amino acids, an amino acid derivative, a protein, a vitamin, a vitaminoid, α-lipoic acid, inositol, a phospholipid, a mineral and a trace element.

10. A preparation according to claim 9, wherein the amino acid derivative is selected from the group consisting of taurine, carnitine and glutathione.

11. A preparation according to claim 1, wherein the preparation additionally contains a sodium salt or a mixture thereof or α-lipoic acid.

12. A preparation according to claim 11, wherein the sodium salt is selected from the group consisting of sodium chloride, sodium sulfate, sodium acetate, sodium adipate, sodium citrate, sodium gluconate, sodium ascorbate, sodium pantothenate, sodium tartrate and sodium lactate.

13. A preparation according to claim 11, wherein the sodium salt is present in a quantity of 0.1 to 75.0 wt. %, relative to the total weight of the preparation.

14. A preparation according to claim 1, wherein the preparation is in a form selected from the group consisting of a powder, a granular product, a pastille, a capsule, a tablet, an effervescent tablet, a solution, a syrup, a gel, a functional foodstuff and a feedstuff.

15. A method comprising administering to a subject the preparation according to claim 1 as a nutritional supplement, a functional foodstuff, a feedstuff additive or as an additive in a cosmetic or dermatological formulation.

16. The method according to claim 15, wherein the cosmetic or dermatological formulation is a cream, a lotion, a spray, a mousse, an aqueous or aqueous ethanolic solution, an impregnation medium for wipes, an anhydrous or hydrous stick or a microemulsion.

17. The method according to claim 15, wherein the cosmetic or dermatological formulation is for topical application.

18. A method for producing the preparation of claim 1, comprising the steps of:
   (a) providing a creatine component, and
   (b) incorporating at least one buffer system.

19. The method of claim 18, further comprising the step of adding at least one member selected from the group consisting of an additional physiologically active compound, a sodium salt, and α-lipoic acid.

* * * * *